United States Patent [19]

Holdaway et al.

[11] Patent Number: 5,156,792
[45] Date of Patent: Oct. 20, 1992

[54] METHOD OF PRODUCING CATHETER ASSEMBLIES FOR PREVENTION OF BLOOD LEAKAGE

[75] Inventors: Richard G. Holdaway, Tampa; Julian E. Cannon, Brandon; Gordon W. Horgen, St. Petersburg; Anthony Y. Van Heugten, Tampa; John W. Egolf, Jr., Palm Harbor, all of Fla.

[73] Assignee: Critikon, Inc., Tampa, Fla.

[21] Appl. No.: 674,831

[22] Filed: Mar. 25, 1991

Related U.S. Application Data

[62] Division of Ser. No. 452,091, Dec. 18, 1989, Pat. No. 5,030,205.

[51] Int. Cl.$^5$ .................. A61M 5/178; B29C 61/08
[52] U.S. Cl. .................. 264/230; 264/249; 264/291; 264/292; 604/164; 604/168
[58] Field of Search .................. 604/164, 165, 168; 264/230, 249, 291, 292

[56] References Cited

U.S. PATENT DOCUMENTS

| | | | |
|---|---|---|---|
| 3,437,788 | 4/1969 | Lingley | 264/230 |
| 3,470,604 | 10/1969 | Zenick | 264/249 |
| 4,129,932 | 12/1978 | Stancati | 264/230 |
| 4,551,292 | 11/1985 | Fletcher et al. | 264/292 |
| 4,652,256 | 3/1987 | Vaillancourt | 604/164 |
| 4,762,516 | 8/1988 | Luther et al. | 604/164 |
| 4,804,733 | 2/1989 | Bataille | 264/230 |
| 4,952,207 | 8/1990 | Lemieux | 604/164 |
| 5,000,740 | 3/1991 | Ducharme | 604/162 |
| 5,008,059 | 4/1991 | Kaeufer et al. | 264/230 |
| 5,030,205 | 7/1991 | Holdaway | 604/164 |

FOREIGN PATENT DOCUMENTS

943845 12/1963 United Kingdom .............. 264/230

Primary Examiner—Jan H. Silbaugh
Assistant Examiner—Brian J. Eastley
Attorney, Agent, or Firm—Paul A. Coletti

[57] ABSTRACT

A catheter is provided which deters the backflow of blood between the insertion needle and the catheter cannula by forming the distal end of the catheter hub so as to restrict the inner diameter of the catheter cannula to a wiping fit with the engaged insertion needle. In a first embodiment the distal end of the catheter hub is pre-formed to its desired final inner dimension. The distal end of the hub is stretched to an oversize condition, the catheter cannula is attached to the hub, and the distal end of the catheter hub is heated, causing a stress relief of the previously stretched hub. The distal end of the catheter hub returns to its pre-formed dimension which will mechanically restrict the diameter of the catheter cannula at that point to form the wiping fit with the engaged needle. In a second embodiment the inner diameter of the distal end of the catheter hub is reduced by inserting the distal end of the hub between the opposing faces of a swaging press, which close to compress the hub in one direction. The degree of closure is controlled by the dimension of at least one of a pair of orthogonally opposing swaging press surfaces, which then close to compress the hub in the orthogonal direction. The distal end of the hub is thus swaged to the desired dimension, and the process advantageously produces a finished product without the production of flash material at the intersection points of the swaging surfaces.

4 Claims, 4 Drawing Sheets

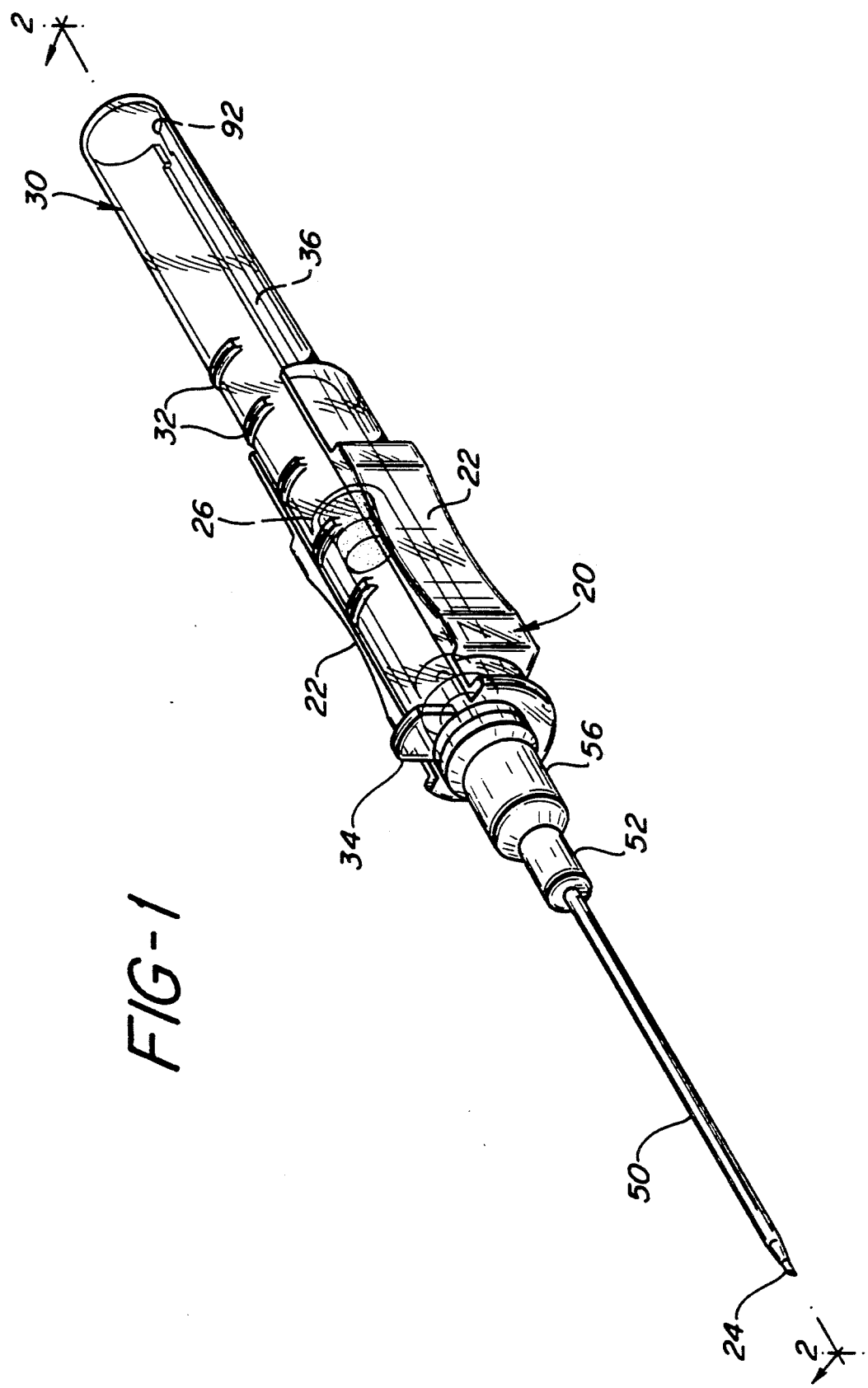

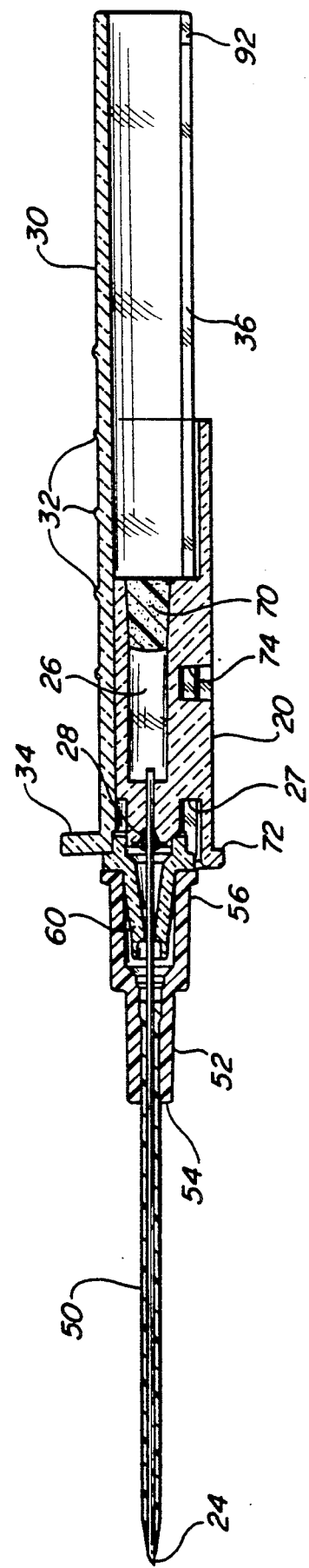

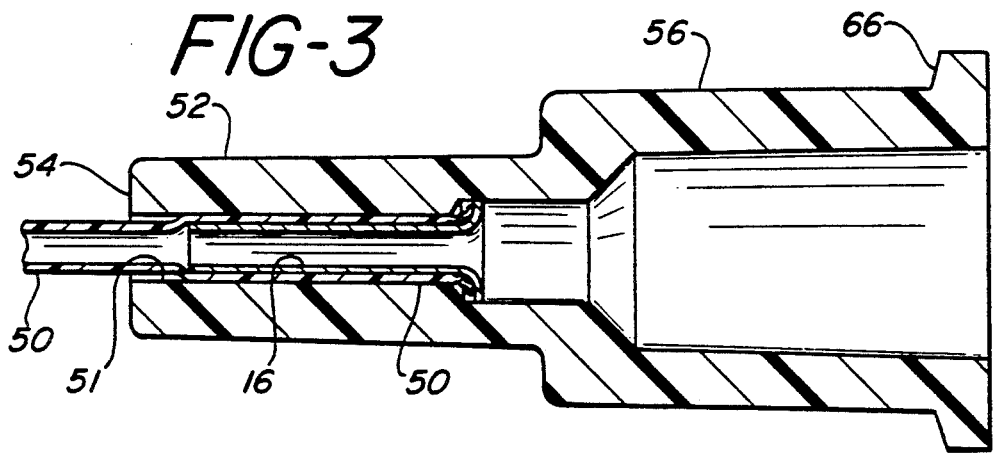
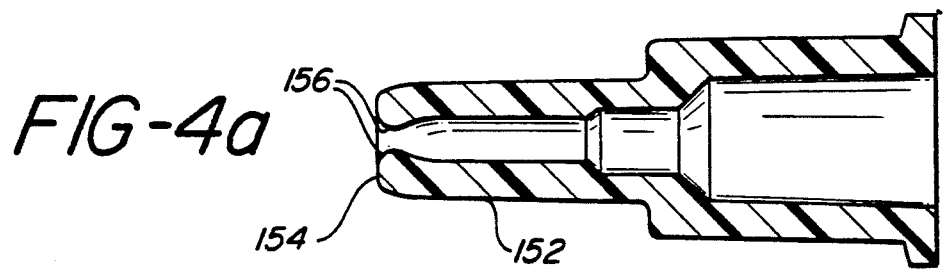
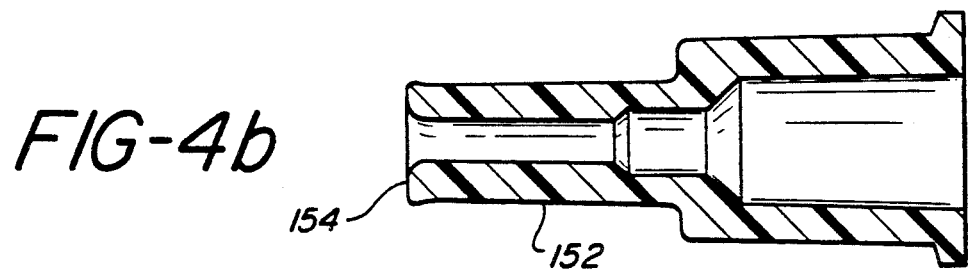
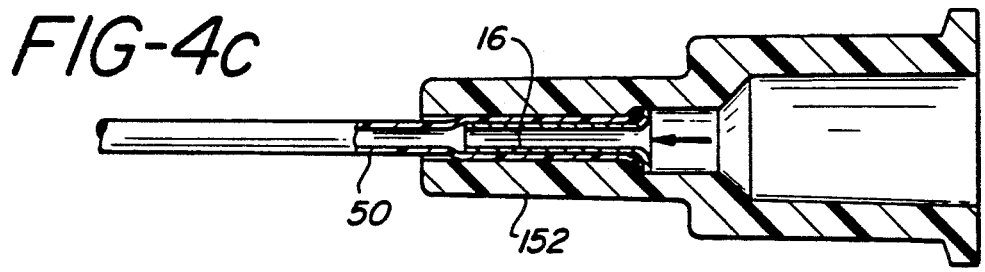
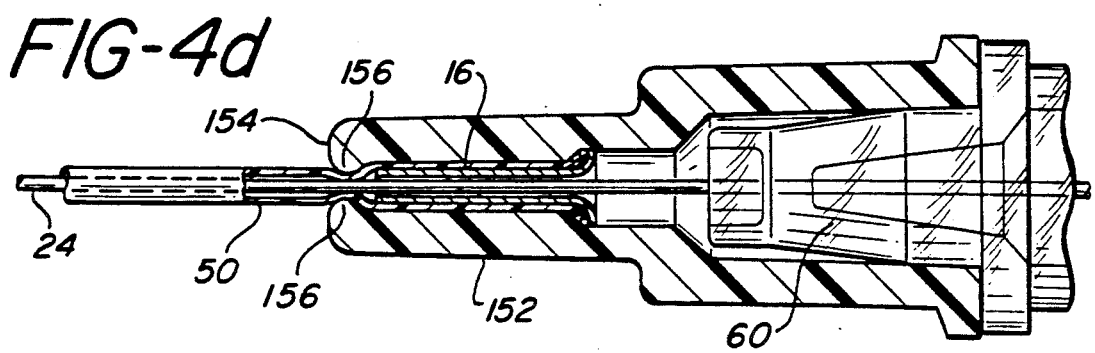

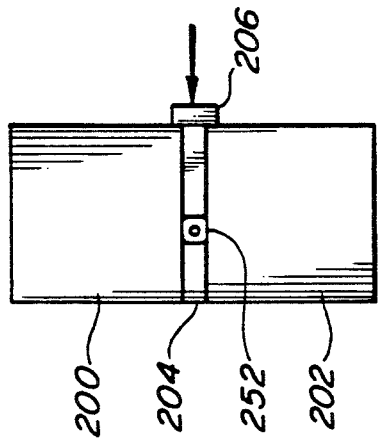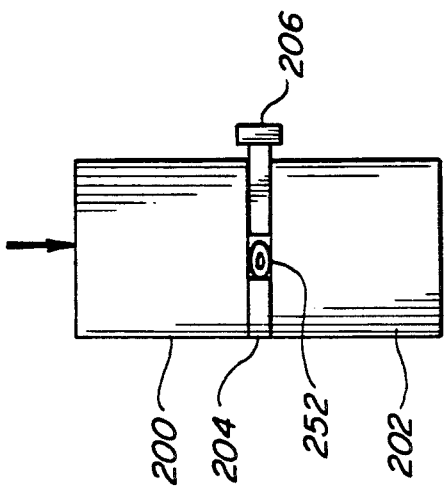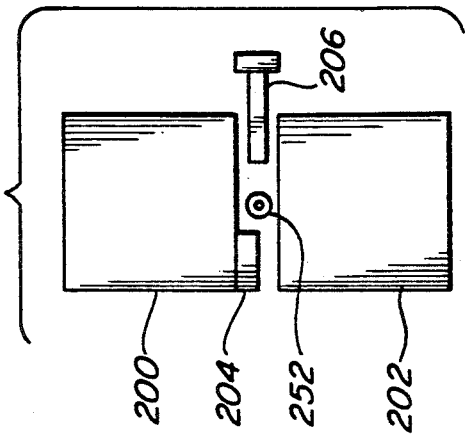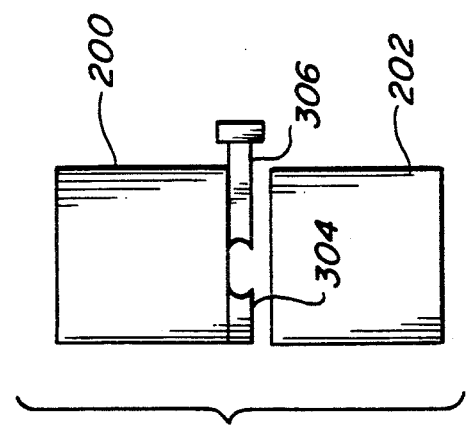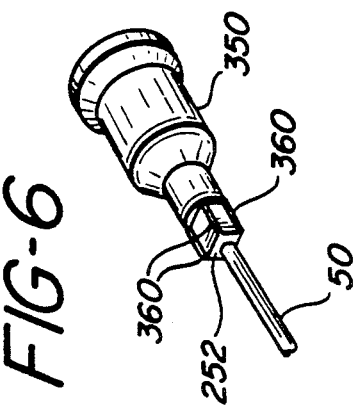

METHOD OF PRODUCING CATHETER ASSEMBLIES FOR PREVENTION OF BLOOD LEAKAGE

This is a division of application Ser. No. 452,091, filed Dec. 18, 1989, now U.S. Pat. No. 5,030,205.

This invention relates to I.V. catheters and, in particular, to the prevention of blood backflow and blood leakage which could result in inadvertent contact with blood during the use of such catheters.

U.S. Pat. No. 4,762,516 (Luther et al.), U. S. patent application Ser. No. 217,246, filed Jul. 11, 1988, and U.S. patent application Ser. No. 335,472, filed Apr. 10, 1989, describe I.V. catheters with needle guards that are designed to Protect medical personnel from inadvertent injury caused by needle sticks subsequent to use of the catheter needle. Such inadvertent needle sticks can result in infection by diseases borne by the blood of the patient from whose vascular system the needle has been previously withdrawn. The catheters described in these patent documents Prevent inadvertent needle sticks by covering the needle tip with a needle guard extending from the needle hub as the needle is withdrawn from the patient's body.

It is not only desirable to protect medical personnel from the hazards of inadvertent needle sticks, but it is further desirable to provide protection from any contact with a patient's blood. Even in the use of one of the aforementioned catheters with needle guards, it is possible for medical personnel to come into contact with a patient's blood due to undesired leakage of blood from the catheter. During insertion of the needle into the vascular system of the patient, the clinician administering the catheter will try to locate the tip of the needle in a vein or artery of the patient. When the needle tip is properly located, there will be a small flow or flash of blood through the hollow needle and into the flash chamber at the proximal end of the needle. The clinician will note this presence of blood in the flash chamber as an indication of proper needle placement. The clinician can then advance the catheter into the vascular system and withdraw the needle from the patient, leaving the catheter cannula in place in the blood vessel.

As the needle tip moves to a location proximal the distal end of the catheter, blood will flow under venous or arterial pressure into the catheter and into the hollow needle. As a consequence thereof, blood may also enter the annular space between the outer wall of the needle and the inner wall of the catheter cannula. The flow of blood in this space toward the catheter hub is herein referred to as backflow. Normally, backflow of blood is of little concern, because the catheter hub is usually quickly connected to a tubing set once the needle is withdrawn from the catheter. However, in the aforementioned catheters with needle guards, the distal nose of the needle guard occupies the catheter hub prior to complete withdrawal of the needle. As the needle guard is extended along the length of the needle toward the needle tip, its extention will carry the catheter hub to simultaneously thread the catheter into the vein or artery of the patient. The termination of this motion will eject the catheter hub from the nose of the guard when the guard reaches it full extention. Thus, if blood backflow into the catheter hub occurs prior to ejection of the catheter hub from the nose of the guard, the needle guard will be contaminated with the patient's blood prior to the release of the catheter hub. It would be desirable to prevent this contamination so that contact by medical personnel with blood on the nose of the needle guard will be prevented.

A technique for reducing the possibility of such blood leakage is described in U.S. patent application Ser. No. 353,276, filed May 17, 1989. As explained in that application, blood leakage between the needle and catheter cannula is retarded by heating and stretching the catheter cannula at a point just distal the distal end of the catheter hub. This process results in the reduction of the inner diameter of the cannula, causing the cannula to hug the needle in the vicinity of this restriction. Blood flow between the needle and cannula will be retarded from reaching the catheter hub as it encounters this restricted section of the catheter cannula. While this technique has been found to effectively retard blood leakage, the technique requires an additional processing step for the catheter cannula after final assembly of the catheter and needle assemblies. It would be desirable, then, to provide this impediment to blood leakage in a manner which obviates the need to perform this additional processing step on the catheter cannula.

In accordance with the principles of the present invention, a catheter is provided which deters the backflow of blood between the insertion needle and the catheter cannula by forming the distal end of the catheter hub so as to restrict the inner diameter of the catheter cannula to a wiping fit with the engaged insertion needle. In a first embodiment the distal end of the catheter hub is pre-formed to its desired final inner dimension. The distal end of the hub is stretched to an oversize condition to facilitate connection of the catheter cannula to the hub. After the catheter and hub have been assembled and engaged by the needle assembly, the distal end of the catheter hub is heated, causing a stress relief of the previously stretched hub. The distal end of the catheter hub will then return to its preformed dimension which will mechanically restrict the diameter of the catheter cannula at that point to form the wiping fit with the engaged needle.

In a second embodiment the inner diameter of the distal end of the catheter hub is reduced through swaging. Following assembly of the catheter hub and cannula, the distal end of the hub is inserted between the opposing faces of a swaging press, which close to compress the hub in one direction. The degree of closure is controlled by the dimension of at least one of a pair of orthogonally opposing swaging press surfaces, which then close to compress the hub in the orthogonal direction. The distal end of the hub is thus swaged to the desired dimension, and the process advantageously produces a finished product without the production of flash material at the intersection points of the swaging surfaces.

In the drawings:

FIG. 1 is a perspective view of an I.V. catheter assembly with needle guard;

FIG. 2 is a cross-sectional view of the catheter assembly of FIG. 1;

FIG. 3 is an enlarged view of the attachment of the catheter cannula to the catheter hub in the catheter assembly of FIGS. 1 and 2;

FIGS. 4a–4d illustrate the production and assembly of a catheter cannula and hub in accordance with the principles of the present invention;

FIGS. 5a–5c illustrate a second embodiment for producing a catheter cannula and hub in accordance with the present invention;

FIG. 6 is a perspective illustration of a prior art catheter cannula and hub;

FIG. 7 is a perspective view of a catheter and hub assembly produced with the apparatus of FIGS. 5a–5c; and FIG. 8 illustrates a modified form of the apparatus of FIGS. 5a–5c.

Referring first to FIG. 1, an I.V. catheter assembly with a needle guard is shown. The assembly includes a needle housing 20 which is semi-tubular in shape and open at the top. Molded on the sides of the needle housing 20 are opposing contoured finger grips 22, one of which is visible in FIG. 1. Located inside the semi-tubular needle housing and extending proximally therefrom is a tubular needle guard 30. On the upper surface of the needle guard are a number of small projections 32 which provide surfaces against which a user may press to fully extend the needle guard. These projections permit a user to extend the needle guard with the index or other finger while holding the catheter assembly with one hand.

A catheter 50 and its catheter hub 52, 56 are mounted on the distal end of the needle guard 30 over the needle 24. The point of the needle 24 is seen to extend from the distal tip of the catheter 50, which may be made of Teflon TM, for example. A push-off tab 34 is seen projecting upward from the needle guard proximal the catheter hub 52. Located on the distal end of the needle guard is a needle guard tip 60, shown in FIG. 2, through which the needle 24 extends. The distal end of the needle 24 is located in a flash chamber 26 which is a part of the needle housing 20.

FIG. 2 is a cross-sectional view of the catheter assembly of FIG. 1. The catheter 50 is seen to extend from the distal end 54 of the catheter hub 52 and is concentric therewith. The catheter may be attached to its hub by any means known in the art, including adhesively or mechanically by means of a metal eyelet. The larger diameter proximal portion 56 of the catheter hub 52 is flanged at its proximal end for connection to an infusion set, and the inner diameter of the proximal portion of the hub is sized to fit over the distal portion of the needle guard tip 60.

The needle 24 is attached to the distal end of the flash chamber 26 of the needle housing with the proximal end of the needle terminating within the chamber. The needle 24 is affixed in place by adhesive 28. The needle extends through the needle guard tip 60, the needle hub 52, and the catheter 50, with the Point of the needle extending from the distal end of the catheter. The rear of the flash chamber 26 is plugged by a microporous plug 70. The needle guard is seen to extend proximal the rear of the needle housing with the needle guard tip 60 affixed to the distal end of the needle guard at the location of the push-off tab 34. The tubular needle guard surrounds the flash chamber 26, with the base 27 of the flash chamber being located in a longitudinal slot 36 at the bottom of the needle guard. As the needle guard slides in the distal direction to cover the needle it is maintained concentric with the needle housing by the concentric tubular construction of the needle housing and needle guard and by the tracking of the base 27 of the flash chamber in the needle guard slot 36.

The flash chamber 26 is seen to be located in the center of the needle housing 20, and is mounted on a rail, or base 27. A rectangular aperture 74 is formed in the base of the housing below the flash chamber 26, and extends upward into the base 27 of the flash chamber.

As explained in U.S. patent application Ser. No. 335,472, the aperture 74 engages the proximal end 92 of the needle guard 30 when the needle guard slides distally to cover the needle, thereby locking the needle guard in its protective position around the needle 24.

Turning now to FIG. 3, the catheter hub 52 of FIGS. 1 and 2 is shown in greater detail. At the proximal end 56 of the hub is a connecting flange for attachment to a tubing set connector. Passing through the distal end 54 of the hub is a central aperture 51. The catheter cannula 50 is attached inside this aperture by a metal sleeve 16 which is flared at its proximal end. The metal sleeve 16 fits inside the catheter cannula to seal the cannula between the sleeve and the aperture 51. The flared end of the sleeve is in a force fit with the aperture wall proximal the cannula to hold the cannula in place within the catheter hub 52.

It may be seen that in the conventional catheter and hub assembly there is an annular space around the catheter cannula 50 at the distal end 54 of the hub. This space permits the cannula to fit loosely around the needle in this area of the assembly, allowing blood to pass between the outer surface of the needle and the inner surface of the cannula. Blood may then pass into the catheter hub proximal the cannula, where it can contaminate the distal end 60 of the engaging needle guard, as may be seen in FIG. 2. A purpose of the present invention is to prevent such blood leakage into the catheter hub, which will be explained with reference to FIGS. 4a–4d.

Referring first to FIG. 4a, a catheter hub 152 is shown. The hub is shown as Produced by a molding process which produces a molded hub with a reduced inside diameter at the distal end 154 of the hub. The distal end of the molded hub bears down on the outer wall of the catheter cannula passing through the hub at 156, thereby pressing the cannula against the inner needle in a wiping fit. The hub is molded with the distal end at the size desired for the cannula and needle diameters and wall thicknesses of the final product.

After the catheter hub 152 is molded as shown in FIG. 4a, it is stretched to the condition shown in FIG. 4b. The catheter hub is stretched by forcing a tapered pin exhibiting a slightly conical shape into the distal end 154. The hub material, which may be polypropylene, polyurethane, or polyolefin, for instance, is stressed by the stretching forces of the tapered pin, which serve to distend the distal end of the hub from its molded shape to the shape shown in FIG. 4b. These stresses will be relieved as described below.

After the catheter hub has been stretched, the catheter cannula 14 is inserted into the hub and is secured in place with the metal sleeve 16. With the distal end of the hub having been stretched to eliminate the narrowing of the distal end, this assembly step is essentially the same as that of a conventional catheter hub. The catheter assembly then appears as shown in FIG. 4c.

After the catheter cannula and hub have been assembled the needle assembly is inserted through the hub 152 and the cannula 14, leaving the catheter hub mounted on the distal end 60 of the needle guard or needle hub, and the needle 24 passing through the hub and cannula 14. At this point the distal end of the catheter hub 152 is heated to a softening temperature. This temperature is chosen in accordance with the material used for the catheter hub and the time of exposure of the hub to the heat, and may be in the range of 300° F. to 450° F. It has been found that reciprocal adjustment can be made between the temperature and the time of exposure of the hub to the heat, with an increase in time of exposure resulting in the use of a lower temperature. The effect of the heating step is to relieve the stresses incurred by the catheter hub material during the stretching step. As a result, the stress-relieved hub will assume its originally molded shape, with the distal end 156 of the hub contracted around the catheter cannula. The cannula is thereby pressed against the inner needle 24 in a wiping fit, which prevents blood leakage between the needle and cannula and into the catheter hub. Typically, the diametric change in the distal end of the catheter hub between the stretched shape and the molded shape is less than 20%.

It has been found through experimentation that direct contact heating is the preferred technique for stress-relieving the hub. In a constructed embodiment the distal end of the hub was inserted into an aperture in a block of Teflon TM heated to the desired temperature. The distal end of the hub was heated and stress-relieved by contact with the surrounding heated Teflon TM of the block.

An alternative technique for achieving the same wiping fit between the catheter cannula and the needle is the swaging process depicted in FIGS. 5a-5c. A swaging press is shown in FIG. 5a comprising a steel block 200 to which is securely attached a smaller steel block or stop 204. The smaller block 204 is dimensioned to permit the desired closure of the press, and may be attached to the larger block 200 as by welding. Opposing the steel blocks 200, 204 from below is another large steel block 202. Located between the two large blocks 200, 202 and in opposition to the smaller block 204 is a moveable compression member 206.

To swage the distal end of the catheter hub around the cannula, the distal end 252 of the hub is placed between the blocks 200 and 202, with the smaller block 204 on one side and the compression member 206 on the other side as shown in FIG. 5a. The press is then closed by moving blocks 200 and 202 toward one another to the limit of closure permitted by the dimension of the block 204. This will compress the hub 252 to the generally oval configuration shown in FIG. 5b. The moveable compression member 206 is then pressed against the hub to the limit permitted by its end stop, which compresses the hub to a square configuration as shown in FIG. 5c. The distal end of the hub is then swaged against the catheter cannula, pressing the cannula against the needle in a wiping fit.

When a catheter hub is swaged in a conventional manner, the result of the process is to leave a small amount of flashing 360 extending from the distal end 352 of the hub 350, as shown in FIG. 6. It has been found that the swaging process shown in FIGS. 5a-5c is effective to swage the distal end 252 of the hub 350 without leaving any flashing, as shown in FIG. 7. Thus, regardless of whether the illustrated swaging process is used to eliminate blood leakage as in the preferred use of the present invention, the process is effective to eliminate further processing necessary to remove the undesired flashing created by the conventional swaging technique.

An alternative swaging press is shown in FIG. 8. This press is similar to that shown in FIGS. 5a-5c, but is modified by the curvature of the side of the smaller block 304 and the opposing end of the compression member 306. As may be appreciated from FIG. 8, the curvature of these two members will cause the finished distal end of the catheter hub to be rounded on two opposing side. It may also be appreciated that the surfaces of the blocks 200 and 202 where the catheter is engaged in the press could also be concave curved to produce a fully rounded distal end of the catheter hub instead of the square configuration shown in FIG. 7.

What is claimed is:

1. A method of producing a catheter assembly for use with a needle assembly in which a catheter cannula is in a wiping fit with a needle extending therethrough comprising the steps of:
   a) forming a catheter hub with an aperture extending therethrough and having an inwardly projecting circumferential protrusion extending from the inner wall of said aperture near the distal end of said hub;
   b) stretching the distal end of said catheter hub in a radially outward direction to substantially reduce the inward extension of said protrusion;
   c) attaching a catheter cannula within said aperture at a location proximal the location of said protrusion;
   d) inserting a needle assembly within said catheter cannula and said catheter hub, said needle assembly containing a needle with an outer diameter intended to engage said catheter cannula inner diameter in a wiping fit; and
   e) heating the distal end of said catheter hub to cause said protrusion to extend inwardly against said catheter cannula, wherein said catheter cannula engages said needle outer diameter in a wiping fit.

2. The method of claim 1, wherein step e) comprises the step of heating the distal end of said catheter hub to a softening temperature to cause said protrusion to extend inwardly against said catheter cannula.

3. The method of claim 2, wherein step b) comprises the step of stretching the distal end of said catheter hub in a radially outward direction to stress the material of said catheter hub to thereby substantially reduce the inward extension of said protrusion;

4. The method of claim 3, wherein step e) comprises the step of heating the distal end of said catheter hub to a softening temperature to stress-relieve the material at the distal end of said catheter hub to thereby cause said protrusion to extend inwardly against said catheter cannula.

* * * * *